United States Patent [19]

Schlegel

[11] 4,172,297

[45] Oct. 30, 1979

[54] ARTIFICIAL IMPLANT LENS

[75] Inventor: Hans-Joachim Schlegel, Bad Homburg, Fed. Rep. of Germany

[73] Assignee: Inprohold Establishment, Vaduz, Liechtenstein

[21] Appl. No.: 887,041

[22] Filed: Mar. 16, 1978

Related U.S. Application Data

[63] Continuation-in-part of Ser. No. 691,712, Jun. 7, 1976, abandoned.

[30] Foreign Application Priority Data

Feb. 24, 1976 [DE] Fed. Rep. of Germany ....... 2607462
Dec. 30, 1977 [DE] Fed. Rep. of Germany ....... 2758912

[51] Int. Cl.$^2$ ............................ A61F 1/16; A61F 1/24
[52] U.S. Cl. .......................................................... 3/13
[58] Field of Search ........................................... 3/13, 1

[56] References Cited

U.S. PATENT DOCUMENTS

| 2,834,023 | 5/1958 | Lieb | 3/13 UX |
|---|---|---|---|
| 3,228,741 | 1/1966 | Becker | 3/13 X |
| 3,711,870 | 1/1973 | Deitrick | 3/13 |
| 3,906,551 | 9/1975 | Otter | 3/13 |
| 3,971,073 | 7/1976 | Richards et al. | 3/13 |
| 3,979,780 | 9/1976 | Boniuk | 3/13 |
| 3,996,627 | 12/1976 | Deeg et al. | 3/13 |

OTHER PUBLICATIONS

"Artiphakia and Aniseikonia" by Richard C. Troutman, American Journal of Ophthalmology, vol. 56, No. 2, Oct. 1963, pp. 630-632.

"A Weightless Iseikonic Intraocular Lens" by Richard D. Binkhorst et al., American Journal of Ophthalmology, vol. 58, No. 1, Jul. 1964, pp. 73-78.

"Optical Properties of Buried Corneal Silicone Prosthesis" by D. Miller et al., American Journal of Ophthalmology, vol. 66, No. 4, Oct. 1968, pp. 633-640.

Primary Examiner—Ronald L. Frinks
Attorney, Agent, or Firm—Erwin S. Teltscher

[57] ABSTRACT

An artificial implant lens for the eye of a living being has a central lens body and front and rear annular discs surrounding the lens body. The annular discs overlap the iris and secure the lens to the iris.

28 Claims, 11 Drawing Figures

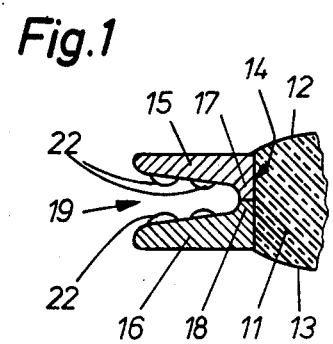
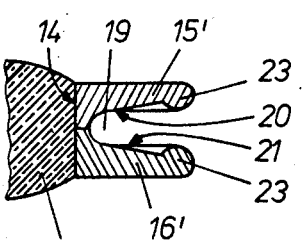
Fig.1　　Fig.2
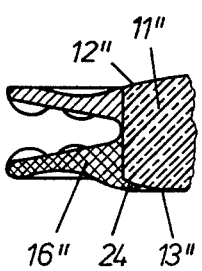
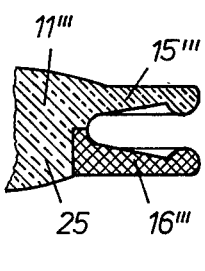
Fig.3　　Fig.4
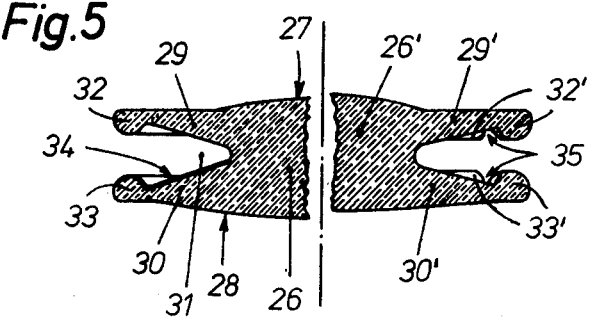
Fig.5　　Fig.6
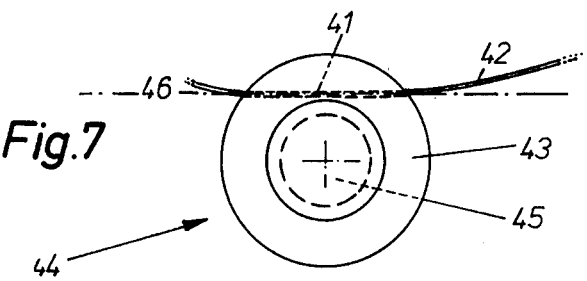
Fig.7

ARTIFICIAL IMPLANT LENS

CROSS REFERENCES TO RELATED APPLICATIONS

This application is a continuation-in-part application of copending application Ser. No. 691,712 filed on June 7, 1976, now abandoned.

BACKGROUND OF THE INVENTION

The invention relates to an implant lens made of transparent material, in particular an elastic and flexible synthetic, plastic material, for example silicone rubber, as a dioptric substitute for a natural lens which has been surgically removed from the eye of a living being. It is fitted with holders which extend radially outwards from the pupil to overlap the iris, and thus to secure the implant lens to the iris.

The nature of the cataract is the clouding of a lens of a living being. The resulting diminution of sight can only be eliminated by surgically removing the lens and then replacing it by a suitable optical material, the most commonly used substitute being the well-known cataract glasses or spectacles; in suitable cases contact lenses are also used, which fit directly against the cornea of the eye. Functionally the best substitute is an artificial lens which is inserted surgically into the eye.

It is therefore an object of the present invention to construct the lenses of the type discussed in such a way that, while retaining all their advantages and properties, they considerably facilitate the difficult task of inserting the lens into the pupil of the iris. A proper lens placement, without any change of position, is thus insured, so that the patient operated on has the same field of vision as had been provided prior to the removal of the natural lens.

This avenue was explored by the Englishman RIDLEY, who in 1949 began implanting a perspex lens into the posterior eye chamber. The expectations and hopes placed in this procedure were not fulfilled however, as experience later showed, which is why it has now been abandoned for some time. In a not insignificant number of cases, the lens slipped out of the posterior chamber and into the vitreous body therebehind. Such lenses, disposed in the wrong place, have the effect of a foreign body in the eye, are not tolerated biologically, and over a period of time represent a substantial danger to the survival of the eye.

A further possibility for a dioptric substitute for the lens removed from the eye was seen in the implantation of plastic lenses in the anterior chamber of the eye. These anterior chamber lenses, as they are called, are not placed in the physiological position, i.e., behind the iris, but at a greater or lesser distance from the latter, in the area of the anterior eye chamber. A wide variety of models of such lenses were designed and used. They came from STRAMPELLI, SCHRECK, WALSER and DANNHEIM, among others. With time, however, it became obvious that these lenses were not tolerated biologically by the eye.

In addition, lenses of transparent plastic became known (BINKHORST, WORST, etc.) which consist of a biconvex or planoconvex disc and have supports of the most varied kinds to hold the lens in place, either in the anterior chamber of the eye or in the plane of the pupil. These lenses are made of polymethacrylates and have wire or plastic loops, usually attached to the back. The plane encompassed by the loop lies behind the back surface of the artificial lens. It is held in place in the eye by insertion of the loops through the pupil of the iris so that they fit against the back surface of the iris. After the surgical insertion of the lens, the pupil is then artificially (medicinally) contracted. The mechanical support of the artificial lens is thus ensured, in that its back surface fits against the anterior surface of the iris, while the supporting loops lie against the posterior surface of the iris. In keeping with their characteristic method of fixation, these lenses are known as "clip-lenses." According to the shape of the differently designed loops, the lens may also be sutured to the iris.

Although the hitherto published results regarding these "iris clip" lenses are relatively favorable, even these do still have decisive disadvantages, which are important and substantial. Because of their specific gravity, every movement of the eye causes these lenses to experience pitching movements, which place an unwelcome mechanical stress or burden on the delicate iris tissue supporting them.

Apart from polymethacrylates, polyamides have also been used as material for such lenses. However, the disadvantage of all these materials is in particular that lenses made from them cannot be sterilized in a surgically perfect manner. To achieve a completely germless state, including killing off bacterial spores, modern surgery uses heat sterilization with hot steam or hot air. In the former of these two methods of sterilization, superheated water vapor at a temperature of 134° C. and a vapor pressure of 2.5 atu (2.5 atu=3.5 at) acts on the material to be sterilized in an autoclave for about 15 minutes; in hot air sterilization, the material to be sterilized is exposed to an artificially circulated air current at 200° C. for about 30 minutes. The lens materials which have hitherto been used cannot stand up to such stresses.

The other possibility, gas sterilization with ethylene oxide at a relatively low temperature of about 55° C., is too risky for implant lenses, because this highly reactive gas, as is generally known, cannot be controllably stored in certain substances, such as plastics, or substances containing plastics.

Sterilization by means of high-energy rays (cathode rays, beta rays, X-ray, gamma rays) must likewise be excluded in the present case, since they may cause molecular structural changes in the plastic bodies; the resultant molecular fragments are not infrequently toxic. It is now known that over a period of time, a substantially increased tendency to corrosion, with subsequent clouding of the material, occurs in radiation-sterilized acrylate lenses (PMMA).

As a result, surgery has inevitably had to make do with subjecting the implant lenses to a chemical liquid sterilization process, i.e., virtually disinfecting them, immediately after their manufacture, and then preserving them in ampoules in more or less suitable fluids. The lenses are taken out of these ampoules immediately before the operation. The limitation of chemical liquid sterilization is due, in the present case, at least by its inability to destroy bacterial spores; also, these chemicals, which are not inert, accumulate in plastic bodies, which they then leave, uncontrollably and over a long period of time, according to an exponential function. This behavior gives cause for concern, particularly for an eye implant.

A further disadvantage of the materials used for the previously known lenses is that they are polymers, where it is not always certain that they are physiologically harmless. It is possible that as a result of incomplete polymerization, residues (residual monomers, oligomers, catalyst residues, hardening residues) may remain in the material and, in time, diffuse into the eye, resulting in tissue injuries, and other inner irritations of the eye which, in themselves, are known. It is true that many implant lenses have been made of materials already discussed and used, but there are no reliable facts to show that these materials are safe beyond all doubt.

SUMMARY OF THE INVENTION

The object of the invention is to construct a lens from a transparent material, in particular plastic, as a substitute for the natural lens which has been surgically removed from the eye of a living being, which does not have the above-mentioned defects of the prior art lenses, which by comparison with the rigid lenses used up to now is also elastic or pliable, to an adequate extent avoids mechanical injury to the adjacent tissues, and which, above all, can be sterilized by the safe methods of medicinal techniques, i.e., by heat sterilization. Furthermore, the dioptrically effective substitute lens is to be so constituted or shaped, that after implantation it is suspended in a virtually weightless state in the aqueous front section of the eye, and thus behaves so as not to have any adverse effect on the iris supporting it, in particular due to its specific gravity; mechanical stresses on the iris are thereby kept to a minimum.

A further object of the present invention is to construct the lens in such a way that a high definition of the image formed on the retina is ensured. It is also to be as far as possible free of those aberrations which are in principle inherent in biconvex lenses. The implant lens should, after all, be of such a nature that in the case of a traumatic eye injury, particularly of the anterior segment of the eyeball, the mere presence of the implant does not lead to a consequent impairment of the entire eye.

To attain this object, according to the present invention, it is proposed to make the lenses of the type discussed from a biologically suitable material, which ensures that the conditions of the above discussed object are used in an optimum way allowed by the present level of research.

An essential feature of the invention is thus the use for the implant lenses of the type concerned of a homogeneous, preferably flexible, crystal-clear material, such as, in particular, silicone rubber or silicone resin, also referred to as organopolysiloxane, whose specific gravity is approximately equal to that of the aqueous humor of the eye, or is only slightly greater than the latter, encompassing, for example, a range of specific gravity from 1.0 to 1.1, and from which, furthermore no physiologically harmful substances are diffused, and which can be sterilized in the only acceptable way, i.e., by heating it.

Out of a plurality of possibly usable plastics, after clarity had been achieved as to the requirements to be met and countless appropriate tests and analyses had been carried out, the specifically named material was found to be to a special degree a suitable and physiologically ideal material, meeting all the requirements. In this connection, recognizing the significance of the specific gravity of the material used in the production of implant lenses plays a decisive role. This is based particularly on the realization of the connection between the defects of prior art lenses and their risks of causing damage.

An important, hitherto unknown disadvantage of the materials usually used for such lenses is that their specific gravity is too high, so that the lenses have a mechanically injurious effect on the iris, to which they are attached, and can thus easily break away from their moorings. On the other hand, a lens body situated in the aqueous humor of the eye, which is made from a material having the specific gravity recommended in the invention, has the decisive advantage that it is subject to considerably less acceleration forces at every movement or tossing motion of the eyeball, and that as a result, the mechanical strain on the iris is correspondingly smaller. Even apparently relatively small differences as regards the density of the material of the implant lens have a considerably greater effect on, or in the operated eye of a patient than was to be expected. This provides an explanation even for post-operative damage to eyes with implant lenses of a previous construction, which up to now had seemed unpredictable, extremely unwelcome, and not infrequently made a renewed operation necessary.

Moreover, to solve further problems within the scope of the object of this invention, it is proposed to construct the implant lenses discussed in such a way that they have a central, dioptrically effective lens body, at the front and the back end of which there is disposed an annular disc which surrounds the lens body and is preferably flexible, between which discs there is formed a ring-shaped space, becoming wider towards its outer edge, to contain the part of the iris which surrounds the pupil.

In order to avoid mechanical injury or irritation to the highly sensitive iris tissue, the edges of the annular discs which face the annular space of the lens should be well rounded-off. It is also of considerable advantage if, near the outer edges of the facing surfaces of the annular discs, extending beyond these and into the annular space, there are disposed oblong stud-shaped or similar projections, in particular an annular ridge, in such a manner that the iris lies in the space between the projections facing one another, so that the lens can support itself against the iris by means of these projections or ridges in its outer peripheral area. Accordingly, the distance between these projections or annular ridges is so dimensioned that the lens is held by the iris in an exact position, either in the anterior chamber of the eye, or, in the preferred way, in the plane of the pupil, so that no further measures are necessary.

It is also essential that the upper surfaces of the annular discs which touch the ring-shaped space of the lens are concavely curved or rounded off in the area of their smaller diameter, in such a way that the transition between them is continuous and smooth, without the appearance of any undesired edge, ridge, etc., which might damage the pupillary part of the iris, since this lies directly against the bent surfaces of the lens body.

Since, for the dioptrical image, only that path of light which penetrates the lens body is of importance, it is sufficient if the curved surfaces at the front of the lens correspond to the diameter of the central lens body, or are marginally larger than the latter, so that observance of this measure results in lenses of minimal thickness and specific gravity.

The lenses according to the invention are, for the sake of practicality, formed in such a way that the central body of the lens, together with at least one of the two annular discs, is made from one piece, so that only the second disc has to be attached to this part. Of course it would also be possible to make the entire lens of the shape concerned in on piece. However, the first-mentioned, two-piece embodiment offers an important advantage in so far as it is possible, according to a further feature of the invention, to make the annular disc facing the inner part of the eye from an opaque material or to cover it with such a material. This has the effect that the lens is given an aperture of a precisely defined diameter. This is above all important if the iris is damaged, torn or deformed, for instance through injury, particularly in the area of the pupil, and the dioptric proportions have thus become defective. If, on the opaque disc there is disposed a flange which narrows the inner diameter and overlaps the edge of the central lens body, this narrows the aperture for the entry of light to the required extent.

It is preferable if the disc disposed at the front end of the central lens body is substantially annular, and includes a torus on a surface thereof adapted to face the iris: the outer diameter of the annular disc preferably exceeds the outer diameter of the torus. The disc disposed at the rear end of the central body is advantageously an elongated cross-bracket formed with a ridge on a surface thereof adapted to face the iris; the ridge is preferably disposed substantially parallel, and close to the circumference of the cross-bracket. The outer diameter of the annular disc is advantageously within the range of 5.5 to 8 mm, and preferably 6 to 7 mm, and the length of the cross-bracket preferably exceeds the diameter of the annular disc by about 2 mm; the diameter of the annular disc is preferably about one and a half times the diameter of the lens body. The torus and the ridge may be continuous or discontinuous. The ridge is preferably formed with discontinuities near corners of the cross-bracket on a portion of its surface facing the lens body. The distance between the rear and front surfaces of the front end and rear end discs is advantageously within the range of 0.4 mm to 0.8 mm, and is preferably about 0.6 mm; the elongated bracket has preferably a substantially convex rear surface.

BRIEF DESCRIPTION OF THE DRAWING

Additional features of implant lenses constructed according to the present invention will be seen from the drawings in conjunction with the description of several embodiments. Thus:

FIGS. 1-6 show side views of various embodiments, according to the present invention, only one half of an axial cross-section being shown in each case, as each lens is axially symmetrical;

FIG. 7 shows a front view of a lens with an embedded support thread;

DESCRIPTION OF THE PREFERRED EMBODIMENTS

Figure 8:
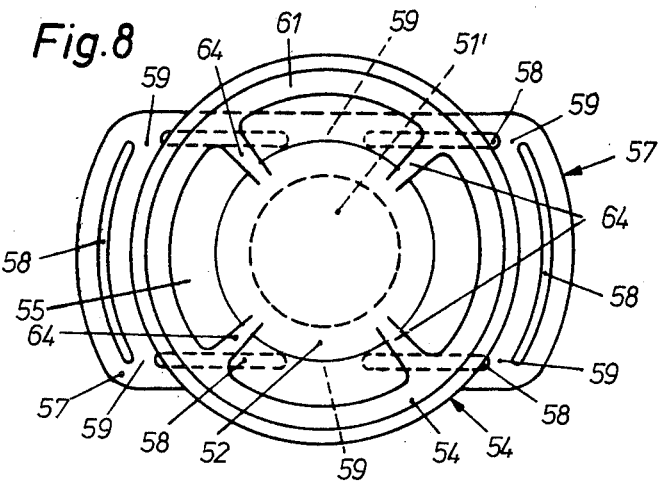
FIG. 8 shows front view of a preferred embodiment of the lens, according to the present invention.

As can be seen from FIGS. 1 and 2, the lens constructed according to the invention includes a central lens body 11, the front face 12 and the back face 13 of which are convexly curved. On the cylindrical peripheral surface 14 of the central lens body 11, two annular discs 15 and 16 are placed, which have at their inner edge a flange, 17 or 18 respectively, which on the one hand increases the contact surface of the annular disc 15 or 16 on the cylindrical peripheral surface 14 of the central lens body 12, and on the other hand determines the distance of the two annular discs 15 and 16 from one another.

Between the two annular discs 15 and 16 there is formed a ring-shaped space 19, which tapers from the outer to the inner diameter of the annular discs. The two facing inner surfaces 20 and 21 are rounded off or curved, both at their outer periphery and in the area of their lesser diameter, or at the flanges 17 and 18 which are fitted to the annular discs, in such a way that no sharp edges are present, that is to say, the curved surfaces join or pass over into one another continuously and are free of edges.

To ensure a good and safe positioning of the lenses after the implantation, i.e., after their insertion into the pupil of the iris of an eye, in which the iris comes to rest with the edge facing the pupil in the annular space 19, there are preferably projections 22, e.g., in the form of oblong studs or the like, on the facing inner surfaces 20 and 21 of the annular discs 15 and 16, extending into the annular space 19, with which the peripheral area of the lens resets against the iris, as is shown by FIG. 1. In the embodiment shown in FIG. 2, instead of the projections 22 there is a circular ridge 23 in the area of the outer edge of the annular discs 15' or 16', which fulfils the same task as the projections 22. These measures ensure that the annular discs 15, 16 do not "stick" to the iris by adhesion, and that the iris is still surrounded by aqueous humor in the eye chambers even in the peripheral area next to the pupil, without the lens being so loosely held to the iris, due to the necessary distance of the inner surfaces 20, 21 or the annular discs 15, 16 from the iris, that the lens is shaky.

In the embodiment, according to FIG. 3, the rear or inner annular disc 16" consists of an opaque material, so that rays falling on the front surface 12" of the lens body 11" only enter the inner part of the eye in so far as the inner diameter of the opaque annular disk 16" allows. If, on the annular disk 16", there is a flange 24, which covers an outer circular area of the rear surface 13" of the lens body 11", this results in a stopping-down or narrowing of the light passage of the lens 11", to the extent to which the flange overlaps the peripheral area of the lens body 11".

A lens consisting of only two parts according to the invention can be seen from FIG. 4. In this, the lens body 11''' and the front annular disc 15''' are made in one piece. On the rear cylindrical part 25 of the lens body 11''', the rear annular disk 16''', again preferably made of an opaque material, is fitted and attached.

The lenses as shown in FIGS. 1 to 6 are preferably made of a silicone rubber or silicone resin, whose specific gravity is only fractionally above that of the aqueous humor of the eye chambers, for example within the range 1.0 to 1.1.

An implant lens made from one mono piece with the features according to the invention, is shown in FIGS. 5 and 6. Both lenses have a central dioptrically operating core 26 the two end surfaces 27 and 28 of which have a convex camber. On both ends of the lens-shaped core 26 there are annular discs 29 or 30 respectively between which the outwardly increasing annular space 31 is situated. Annular toruses 32, 33 are situated on the annular discs 29, 30 on surfaces facing each other. With the lens according to FIG. 5, the surface facing the iris, of the rear or inner annular disc 30 or of the annular disc 30 lying behind the iris, is provided with an opaque, e.g., blackcolored layer 34, in order to achieve a screening of the light penetrating through the lens. With the lens according to FIG. 6, the annular toruses 32' or 33' on the annular discs 29', 30' are not continuous, rather they are provided with interruptions 35.

Although the lenses constructed according to the present invention generally require no further fastening or fixation, since they are adequately held in place in the pupillary aperture of the iris of the pupil, it may at times be desired, or particularly after injury to the iris of the pupil necessary, to secure the lens which has been inserted into the operated eye of a patient additionally in its predetermined position.

In lenses which were hitherto commonly used, such an attachment is usually made by suturing to the highly sensitive and mechanically not very stable iris. In consequence of the above mentioned drawbacks of the prior art lenses, undesirable harm may be caused to the iris, and in the worst case, the suture may come apart or tear out.

These disadvantages can be avoided, according to the present invention, by fixing the two ends of a thread or wire attached to the lens in that part of the sclera through which the incision for the eye operation was made. The grafting in of this supporting thread as the wound heals results in a particularly stable fixation.

For this purpose, in a further embodiment of the lenses according to the invention, a part 41 of a surgical connecting material (yarn, thread or wire) 42 is embedded in the material of the front disk 43 of the lens 44, outside the path of light of the peripheral rays penetrating the lens body 45, approximately along a secant 46. This thread 42 must of necessity be made from a material which, over a long period inside the eye chamber, is not subject to any kind of corrosion or similar fluctuations, and does not alter its physical/mechanical properties. It is therefore proposed to preferably use a silk or similar thread, which, particularly when embedded in a silicone rubber or silicone resin material, is impregnated and/or coated with the same material in such a way that its flexibility and elasticity is not impaired. A thread prepared in such a way ensures absolutely safe anchoring in the material of the lens disc 43.

Another form or embodiment of the implant lens has been found to be particularly expedient and advantageous. This form or embodiment has important advantages especially for handling by the operating surgeon when inserting it into the pupil opening of the iris. Due to the smallness of the objects, i.e., of the parts of the human eye concerned, and of the implant lens itself, the operation can only be performed with instruments, and even then only under a stereo-microscope. Since, in addition, the material of the implant lens is itself highly transparent and the space between the annular discs or supporting elements supporting the lens, and in which the inner edge of the iris comes to rest, is only very narrow and measures considerably less than 1 mm, the task of inserting the lens is considerably simplified by the arrangement of a cross-bracket on the rear, dorsal side of the lens, extending beyond the edge of the front, ventral annular disc, and the position of the lens in the pupil of the iris is also substantially improved thereby.

Figure 9:
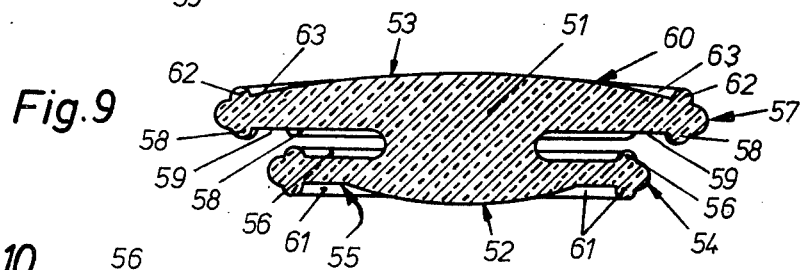
FIG. 9 is a section of the lens along the lines IX—IX of FIG. 8.
Figure 10:
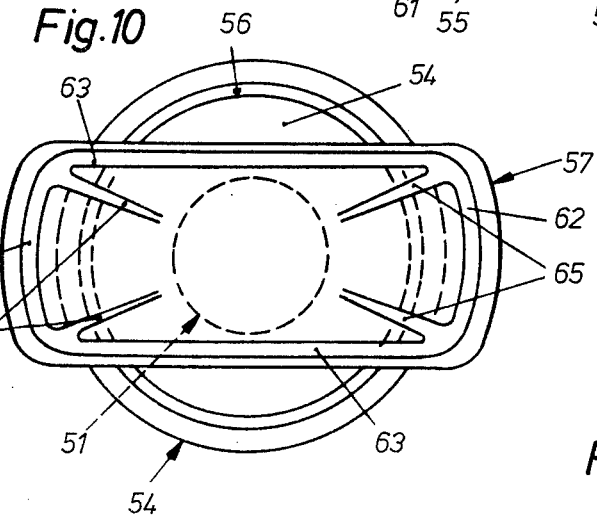
FIG. 10 is a rear view of a preferred embodiment of the lens.

FIGS. 8 to 10 show a preferred embodiment of the implant lens, according to the present invention, which is described in detail below.

The implant lens has a central, cylindrical lens body 51, whose front and rear surfaces 52 and 53 respectively are convexly curved. At the front, ventral end of the lens body 51 is an annular disc 54, whose outer diameter measures approx. 5.5 to 8 mm, preferably approx. 6 to 7 mm. The convexly curved front surface 52 of the lens body 11 merges at the sides into the surface 55 of the annular disc 54. The outer diameter of this convex curve is slightly larger than the diameter of the cylindrical lens body, so as also to permit passage of peripheral rays, into the lens body at a wide angle of incidence.

On the inner side of the annular disc, which faces the iris, there is a torus 56, which may be continuous or partly discontinuous, and which prevents the edge of the iris from resting fully on a corresponding lens surface. It is in fact desirable to maintain a certain space in which there is aqueous humor to keep the iris constantly moist. At the rear, dorsal end of the dioptrically effective lens body there is an approximately rectangular, oval or elliptically-shaped cross bracket 57, whose length exceeds, preferably by about 2 mm, the diameter of the front, ventral annular disc, and whose width corresponds approximately to one and a half times the diameter of the lens body 51. On its side facing the iris, and parallel to its outer edges, the cross-bracket has a continuous or partly discontinuous ridge 58. Preferably, the ridge 58 is formed with discontinuities 59 in the center of the longitudinal edges, and at the corners of the rectangular cross-bracket 57, or at corresponding positions of a differently shaped cross bracket, these discontinuities likewise serving to supply the capillary gap between the iris and the surface of the cross-bracket which is facing the iris with aqueous humor. The entire rear, dorsal surface 60 of the cross bracket 57 has a spherically convex curvature, so that the stability of the cross-bracket is improved thereby. Although this causes the cross-bracket to be somewhat thicker, in view of the preferred material used, i.e., silicone rubber, this is not disadvantageous, as the specific gravity of this material in relation to that of the aqueous humor is so favorable, that the slightly increased mass of the material does not have a significantly increased gravitational effect.

If due to the flexibility of the material used, a further improvement in stiffness of the annular disc 54 or the cross bracket 57 is required, it is advantageous to provide toruses 61 or 62 and 63 on the outer surfaces, which run closely along the outer edges. Radial ridges 64 and 65 can possibly be provided in addition, in order to ensure the required stiffness of the parts of the implant lens in question.

Figure 11:
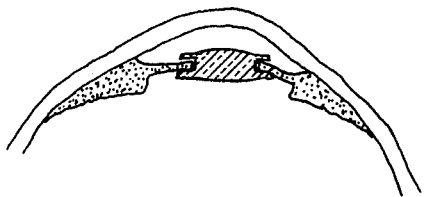
FIG. 11 illustrates an implanted lens in the eye.

FIG. 11 clearly illustrates how the implant lens is placed in the eye by an operation after removal of the natural lens.

The foregoing is considered as illustrative only of the principles of the present invention; since numerous modifications and changes will readily occur to those skilled in the art, it is not intended to limit the invention to the exact construction and operation shown and described, the appended claims encompassing any suitable modifications and equivalents of the present invention.

What is claimed is:

1. A lens of transparent material as a substitute for a surgically removed natural lens in the eye of a living being, comprising:
   a central lens body having front and rear ends, and
   two discs adapted to overlap the edge of the iris which surrounds the pupil, for being attached to the iris, and disposed at said front and rear ends of said central lens body, respectively, an annular space being formed between said discs, said space widening towards its outer edge for receiving the pupil edge of the iris.

2. A lens according to claim 1, wherein said material includes a homogeneous, preferably flexible and elastic crystal-clear plastic material having a temperature stability of at least 200° C., being adapted to be physiologically neutral to tissues, and having a specific gravity equal to, or slightly exceeding the specific gravity of the aqueous humor of the human eye.

3. A lens according to claim 2, wherein said specific gravity is within the range of 1.0 to 1.1.

4. A lens according to claim 1, wherein said lens body has convexly curved faces, and wherein said discs are substantially annular and rounded out in an area bordering said space and near said lens body.

5. A lens according to claim 4 wherein said discs are concavely curved in an area bordering said space and near said lens body, and have a continuous and ridgeless transition.

6. A lens according to claim 4 wherein said lens body has on optically effective region of a predetermined diameter, and wherein at least one convexly curved face has a diameter equal to at least the diameter of said lens body.

7. A lens according to claim 1 wherein said discs have two facing surfaces, a projection being disposed at least on one of said surfaces and extending therebeyond into said space.

8. A lens according to claim 7, wherein said projection includes an annular ridge.

9. A lens according to claim 7 wherein said projection includes an interrupted annular ridge.

10. A lens according to claim 1, wherein the surfaces of said discs facing the annular space are rounded off at their outer edges.

11. A lens according to claim 1, wherein said lens body and said discs are integral.

12. A lens according to claim 1, wherein said lens body an said discs include a plurality of pieces.

13. A lens according to claim 1, wherein the rear disc for lying behind the iris is composed of an opaque material.

14. A lens according to claim 1, wherein in the rear disc is covered with an opaque material coating.

15. A lens according to claim 1, wherein the rear annular disc includes means for reducing the escape of light from said lens body.

16. A lens according to claim 15, wherein the light-reducing means includes a flange having the shape of a diaphragm ring.

17. A lens according to claim 1, wherein said lens body has an optically effective part including a front disc and further comprising a thread of surgically durable material embedded in a region of said front disc disposed substantially beyond the path of light rays penetrating said optically effective part of said lens body.

18. A lens according to claim 17, wherein said front disc is composed of a predetermined material, and wherein said thread is impregnated or coated with said predetermined material.

19. A lens according to claim 1, wherein said material is silicone rubber.

20. A lens according to claim 1, wherein the disc disposed at said front end of said central lens body is substantially annular, and includes a torus on a surface thereof adapted to face the iris, the outer diameter of the annular disc exceeding the outer diameter of said torus, and wherein the disc disposed at the rear end of said central body is an elongated cross-bracket formed with a ridge on a surface thereof adapted to face the iris, said ridge being disposed substantially parallel, and close to the circumference of said cross-bracket.

21. A lens according to claim 20, wherein said torus and said ridge are discontinuous.

22. A lens according to claim 20, wherein said cross-bracket has corners and said ridge is formed with discontinuities near said corners and on a portion of the cross-bracket facing said lens body.

23. A lens according to claim 20, wherein the outer diameter of said annular disc is within the range of 5.5 to 8 mm, wherein the length of said cross-bracket exceeds the diameter of said annular disc by about 2 mm, and wherein the diameter of said annular disc is about one and a half times the diameter of said lens body.

24. A lens according to claim 20, wherein the disc disposed at said front end has a rear surface and the disc disposed at said rear end has a front surface, the distance between said rear and front surfaces being within the range of 0.4 mm to 0.8 mm.

25. A lens according to claim 20, wherein radial ridges are arranged on the outer surface of the annular disc.

26. A lens according to claim 20, wherein radial ridges are arranged on the outer surface of the cross-bracket on its outer periphery.

27. A lens according to claim 20, wherein said elongated bracket has a substantially convex rear surface.

28. A lens according to any one of claims 20 through 27, wherein said material is silicone rubber.

* * * * *